(12) United States Patent
Stoerkel et al.

(10) Patent No.: US 8,522,390 B2
(45) Date of Patent: Sep. 3, 2013

(54) ORAL CLEANING SECTION

(75) Inventors: Ulrich Stoerkel, Bad Nauheim (DE);
Thomas Fritsch, Eppstein (DE);
Michael Stolper, Eschborn (DE)

(73) Assignee: Braun GmbH, Kronberg (DE)

( * ) Notice: Subject to any disclaimer, the term of this patent is extended or adjusted under 35 U.S.C. 154(b) by 311 days.

(21) Appl. No.: 12/967,117

(22) Filed: Dec. 14, 2010

(65) Prior Publication Data
US 2011/0138561 A1   Jun. 16, 2011

(30) Foreign Application Priority Data

Dec. 15, 2009  (EP) ................................ 09015485

(51) Int. Cl.
*A47K 7/02*   (2006.01)

(52) U.S. Cl.
USPC ............................... 15/221; 15/21.2; 15/22.2

(58) Field of Classification Search
USPC ........................................ 15/21.1, 22.1, 22.2
See application file for complete search history.

(56) References Cited

U.S. PATENT DOCUMENTS

| | | | |
|---|---|---|---|
| 5,186,627 A * | 2/1993 | Amit et al. ..................... | 433/216 |
| 6,588,042 B2 | 7/2003 | Fritsch et al. | |
| 8,032,964 B2 | 10/2011 | Farrell et al. | |
| 2003/0226223 A1 | 12/2003 | Chan | |
| 2011/0219558 A1 * | 9/2011 | Vitt et al. ..................... | 15/167.1 |
| 2012/0174328 A1 * | 7/2012 | Moskovich et al. ............ | 15/106 |

FOREIGN PATENT DOCUMENTS

| | | |
|---|---|---|
| DE | 35 44 256 A1 | 6/1987 |
| EP | 0 500 537 B1 | 11/1994 |
| EP | 1 023 001 B1 | 12/2003 |
| EP | 2 107 892 A1 | 10/2009 |
| GB | 2359739 A | 9/2001 |
| WO | WO 2010/007358 A2 | 1/2010 |

OTHER PUBLICATIONS

International Search Rpt. For PCT/IB2010/055817 dated Nov. 7, 2011.

* cited by examiner

*Primary Examiner* — Lee D Wilson
*Assistant Examiner* — Shantese McDonald
(74) *Attorney, Agent, or Firm* — John P. Colbert (57) ABSTRACT

An oral cleaning section is disclosed. The oral cleaning section includes a first carrier having a cleaning side on which at least a first cleaning element is mounted and a second side opposite to the cleaning side, a second carrier having a cleaning side on which at least a second cleaning element is mounted, at least one aperture being formed in the first carrier such that the aperture extends from the cleaning side to the second side, with the second cleaning element extending through the aperture. The second carrier is arranged underneath the first carrier such that the cleaning side of the second carrier is underneath the second side of the first carrier and laterally extends beyond the aperture in at least a first direction. The first carrier and the second carrier are arranged for relative movement to each other.

14 Claims, 5 Drawing Sheets

ORAL CLEANING SECTION

CROSS REFERENCE TO RELATED APPLICATIONS

This application claim the benefit of EP Patent Application No. 09015485.7 filed on Dec. 15, 2009.

FIELD OF THE INVENTION

The present disclosure relates generally to an oral cleaning section. More particularly, the present disclosure relates to an oral cleaning section that has a first carrier on which at least a first cleaning element is mounted and a second carrier on which at least a second cleaning element is mounted.

BACKGROUND OF THE INVENTION

US 2008/0307591 A1 discloses as an oral cleaning section a brush section for use with an electric toothbrush. The brush section has a brush head portion that supports a first plurality of contact elements and a movable contact element holder that supports a second plurality of contact elements. In some embodiments, multiple rows of the first plurality of contact elements are separated by a row or rows of the second plurality of contact elements.

Each of the support structures must have a width that allows mounting of the contact elements without breaking or unduly deforming the support structures, which does not allow a high density of contact elements perpendicular to the row direction, specifically when the rows of contact elements of the first and second plurality of contact elements are alternately arranged.

Thus it is a desire to provide an oral cleaning section that enables a high density of first and second oral cleaning elements while allowing for a relative movement of the first and second cleaning elements relative to each other.

SUMMARY OF THE INVENTION

In one embodiment, an oral cleaning section is provided. The oral cleaning section includes a first carrier having a cleaning side on which at least a first cleaning element is mounted and a second side opposite to the cleaning side; a second carrier having a cleaning side on which at least a second cleaning element is mounted; at least one aperture being formed in the first carrier such that the aperture extends from the cleaning side to the second side, with the second cleaning element extending through the aperture. The second carrier is arranged underneath the first carrier such that the cleaning side of the second carrier is underneath the second side of the first carrier and laterally extends beyond the aperture in at least a first direction. The first carrier and the second carrier are arranged for relative movement to each other.

In another embodiment, an oral cleaning section is provided. The oral cleaning section includes a mounting structure and a second carrier having a cleaning side on which at least a cleaning element is mounted and a second side being opposite to the cleaning side, which second side is exposed so that it can be brought into contact with tissue in an oral cavity.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, the oral cleaning section includes a first carrier that has a cleaning side on which at least a first cleaning element is mounted and a second carrier having a cleaning side on which at least a second cleaning element is mounted. At least one aperture is provided in the first carrier. The second carrier is arranged underneath the first carrier with respect to the cleaning side of the first carrier (i.e. the first and the second carrier are arranged on top of each other such that the cleaning side of the first carrier defines the outmost lying side of the arrangement that is intended for facing an oral site to be cleaned). Further, the cleaning side of the second carrier laterally extends beyond the aperture, i.e. the second carrier overlaps with the first carrier at least in a lateral direction, which is enabled as the carriers (not only their mounting surfaces) are arranged underneath each other. The second cleaning element extends through the aperture. The first carrier and the second carrier are arranged for relative movement to each other. As the first carrier and the second carrier are arranged on top of each other this allows for overlap in the wall thickness needed for mounting the first and the second cleaning elements on the first and second carrier, respectively. This leads to a higher cleaning element density in the formed cleaning element field as the first and second cleaning elements can be brought closer together with the proposed arrangement than in an arrangement as known from US 2008/0307591 A1. The first and/or the second cleaning element or cleaning elements may be realized by bristles or by bristle tufts, but this shall not mean that it should be excluded that cleaning elements can be realized as for example. soft elastomeric cleaning structures.

In an embodiment of the oral cleaning section, the first carrier and the second carrier are movably coupled to each other, for example, the second carrier can be supported by the first carrier so as to enable the relative movement in a low volume realization. In another embodiment of the oral cleaning section, the second carrier is arranged for an oscillatory wiping motion around a longitudinal axis that is essentially parallel to a longitudinal extension axis of the oral cleaning section. Thus, in operation, when the oral cleaning section extends into the oral cavity, the second cleaning element or the second cleaning elements perform an oscillatory wiping motion similar to the wiping motion a user of a manual toothbrush would utilize to clean the teeth, without the need for the user to have to move the oral cleaning section actively.

In a further embodiment of the oral cleaning section, the oral cleaning section includes a coupling element for transferring motion induced by a drive to at least one of the first or second carrier. In an even further embodiment of the oral cleaning section, the first carrier is arranged to at least partially envelope the second carrier. The first carrier may be designed to house the second carrier in an internal cavity. In particular, the second carrier may have a second side that is exposed at the back of the oral cleaning section such that it can be brought into contact with tissue present in the oral cavity. The second side may have a texture, i.e. a roughness or structures suitable for cleaning the tongue.

In this respect, according to an aspect of the present disclosure, an oral cleaning section has a mounting structure and a second carrier having a cleaning side on which at least a cleaning element is mounted and a second side being opposite to the cleaning side, which second side is exposed so that it can be brought into contact with tissue present in an oral cavity, for example, a tongue, where the second side may be textured.

In yet another embodiment of the oral cleaning section, at least a first row of first cleaning elements is mounted on the first carrier and at least a second row of second cleaning elements is mounted on the second carrier, with the second row of second cleaning elements extending through the aperture. Several apertures may be formed in the first carrier such that one of the several second rows of second cleaning elements extend through each one of the apertures and several first rows of first cleaning elements may be mounted on the first carrier such that the first rows and the second rows are alternately arranged. In such an embodiment, a high density of cleaning elements in a direction perpendicular to the row extension direction can be achieved.

In an embodiment of the oral cleaning section, the distance between an outer edge of the first cleaning element and an outer edge of the second cleaning element is less than about 1.6 mm, for example, less than about 1.4 mm or less than about 1.2 mm and in particular the distance may be around about 1.0 mm. This can only be achieved if the wall thickness required for mounting overlaps, which is allowed because of the stacked arrangement of the first and second carriers.

In another embodiment of the oral cleaning section, a third carrier concludes the oral cleaning section at a distal end (where the distal end is the end that lies away from a handle section of the oral cleaning device in an attached state, i.e. the proximal end of the cleaning section is the end that is intended for coupling to the handle section), with the third carrier being fixedly connected with the second carrier. In such an arrangement, the third carrier would perform the same relative motion to the first carrier as the second carrier, for example, an oscillatory wiping motion around a longitudinal axis. The specific arrangement of a carrier arranged so as to conclude the oral cleaning section can be considered as a novelty in itself that is independent from the other features previously discussed. The respective carrier may in particular be arranged for an oscillatory wiping motion around a longitudinal axis that is parallel to the longitudinal extension axis of the oral cleaning section.

The oral cleaning section may be realized as a replacement brush-head for detachable connection to a handle section of a toothbrush, in particular an electric toothbrush.

Figure 1A:
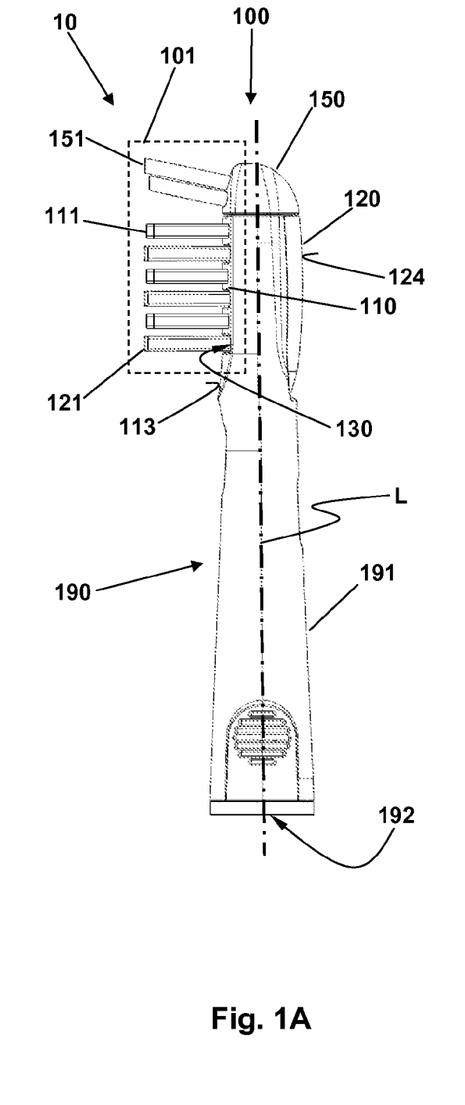
FIG. 1A is a side view onto an oral cleaning section as proposed that is realized as a detachable brush head for an electric toothbrush.

The present disclosure is further concerned with an oral cleaning device (such as an electric toothbrush or a manual toothbrush) in which an oral cleaning section as proposed is utilized. In case the oral cleaning device is realized as a manual toothbrush, the oral cleaning section may be integral with a handle of the manual toothbrush. The oral cleaning device may comprise a handle section to which the oral cleaning section is detachably attached. In a manual toothbrush, provision may be made for an actuator that can be used to move the second carrier. Referring now to FIG. 1A is a side view onto an exemplary embodiment of an oral cleaning section 10. In the shown embodiment, the oral cleaning section 10 is realized as a detachable brush head for detachable connection to a handle section of an oral cleaning device (in FIG. 6 an exemplary oral cleaning device is shown that is realized as an electric toothbrush). The oral cleaning section 10 comprises a head part 100 and a tubular mounting structure 190. The head part 100 of the oral cleaning section 10 comprises a cleaning element field 101 (here realized as a bristle tuft field) that extends from the head part 100 essentially into a direction perpendicular to the longitudinal extension direction L of the oral cleaning section, as is usual in the art to enable effective cleaning of an area in the oral cavity such as the teeth, the gums, the mucosa, or the tongue surface. In another embodiment, the oral cleaning section is integral with a handle section of an (battery-operated or rechargeable) electric toothbrush or a manual toothbrush.

The mounting structure 190 comprises a tube 191 that is slightly tapered towards the head part 100 and is realized as being integral with a first carrier 110 of the head part 100 of the oral cleaning section 10. The tube 191 has an opening 192 at the end distal to the head part 100 for accommodating, for example, a driving shaft extending from the handle section of the oral cleaning device and for detachably mounting the oral cleaning section to a handle section of an oral cleaning device.

The first carrier 110 has a cleaning side 113 on which first cleaning elements 111 (here realized as bristle tufts) are mounted, which first cleaning elements 111 are part of the cleaning element field 101. The first carrier 110 is an integral part of the oral cleaning section 10 and can be manufactured, for example, by a single plastic injection moulding process together with the tube 191. The first cleaning elements 111 may be considered as static cleaning elements of the oral cleaning section 10 as they are fixed in relation to the mounting structure 190. When mounted onto the handle section of the oral cleaning device, the first carrier 110 may not be driven during operation but may remain static with respect to the tube 191 and the handle section. In another embodiment, the whole cleaning section 10 is additionally driven into a motion (e.g. a reciprocation oscillation in longitudinal extension direction L). The first cleaning elements 111 are then still fixed (i.e. static) with respect to the mounting structure 190.

The head part 100 further comprises a second carrier 120 that is a movably supported part of the oral cleaning section 10 (as will be further discussed with reference to FIG. 2 and FIG. 4). Second cleaning elements 121 (here also realized as bristle tufts) are mounted on the cleaning side of the second carrier 120, which second cleaning elements 121 extend through apertures 130 formed in the first carrier 110 so that the second cleaning elements 121 are here also part of the cleaning element field 101 and are arranged in close vicinity to the first cleaning elements 111. The first and second cleaning elements 111 and 121 form the cleaning element field 101 (here a bristle tuft field) as is known from brush heads of manual or electric toothbrushes. When attached to a handle section of an electric oral cleaning device, the second carrier 120 may be coupled to the drive shaft of the electric oral cleaning device. During operation the second carrier 120 would then be set into an arcuate oscillatory motion or oscillatory wiping motion or sweeping motion around a longitudinal axis that is essentially parallel to a longitudinal extension axis L of the oral cleaning section 10. In operation, the second cleaning elements 121 will then move relative to the first cleaning elements 111 (which will here remain static with respect to the mounting structure 190). Generally, the first carrier 110 and the second carrier 120 are arranged for relative movement to each other, hence in another embodiment, the first carrier and the second carrier are both arranged for relative movement with respect to each other and with respect to the mounting structure. The oscillatory wiping motion of the second cleaning elements 121 around the longitudinal axis is very similar to the motion a user would perform with a manual oral cleaning device, for example, a manual toothbrush. Hence, the shown embodiment of an oral cleaning section 10 as proposed supports the feeling of a natural motion that may be preferred by some users in contrast to other motions the brush head may perform.

The second carrier 120 has a second side 124 that extends through an opening in the backside of the head part 100 (i.e. the first carrier is designed in such a way that it covers the cleaning side of the second carrier 120 and also partially envelopes the second carrier 120—one may say that the second carrier 120 is here partially housed in the first carrier 110—such that the second side 124 of the second carrier 120 is exposed). Hence, in operation not only the second cleaning elements 121 move with respect to the mounting structure 191, also the second side 124 of the second carrier 120 moves and thus provides a moving surface on the back side of the head part 100. This can be used to, for example, provide a tongue cleaner structure suitable to clean the tongue by making the second side 124 of the second carrier 120 textured (for example, by making the second side 124 rough or by providing structures on the backside; the texture may be provide by a further material layer, for example, an elastomeric material, applied to the second side 124).

In the shown exemplary embodiment, the head part 100 further comprises a third carrier 150 concluding the distal end of the oral cleaning section 10. The third carrier 150 has a cleaning side on which third cleaning elements 151 (here again realized as bristle tufts) are mounted. The extension direction of the third cleaning elements 151 is somewhat (outwards) inclined with respect to the cleaning side of the oral cleaning section 10, whereas the extension direction of the first and second cleaning elements 111 and 121 is essentially normal to the cleaning side of the oral cleaning section 10. In the shown embodiment, the third carrier 150 is integral with the second carrier 120. The provision of such a movable carrier that concludes the distal end of the oral cleaning section and also performs an oscillatory wiping motion around a longitudinal axis that is essentially parallel to the longitudinal extension axis of the oral cleaning section 10 is an independent novelty in itself and is further considered as an optional feature in the context of the present disclosure.

In case the first or second or third cleaning elements 111, 121, or 151, respectively, are realized as bristle tufts, they can be mounted to the first, second, or third carriers 110, 120, or 150, respectively, in a manner as is known in the art, e.g. via stapling (anchoring), anchor free tufting (AFT), or an in-moulding process. Instead of bristle or bristle tufts, at least some of the cleaning elements could, for example, be realized as soft and flexible elastomeric fingers for massaging and softly removing debris from oral tissue or as thin and flexible flaps for cleaning in the interdental cavities etc.

Figure 1B:
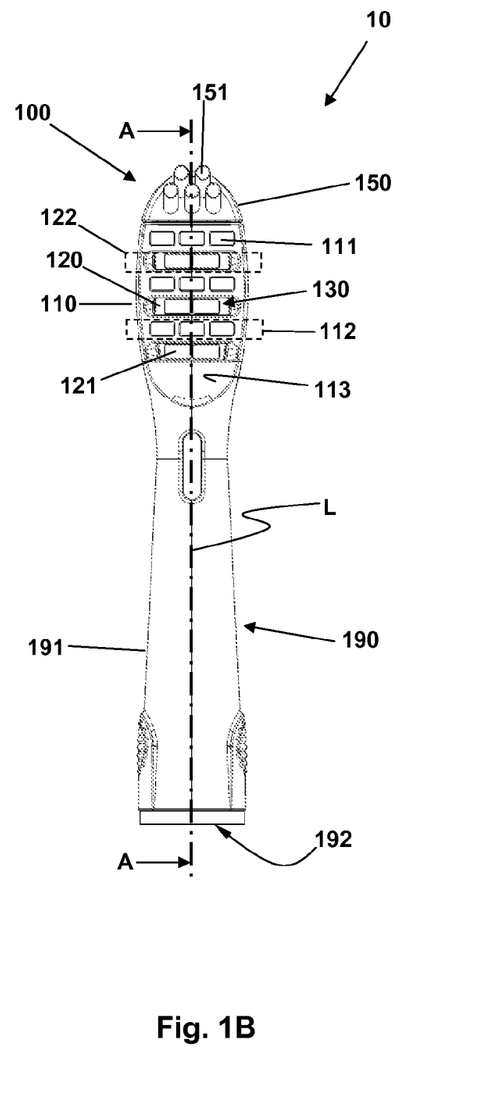
FIG. 1B is a frontal view onto the cleaning side of the oral cleaning section shown in FIG. 1A.

FIG. 1B is a frontal view onto the cleaning side 113 of the oral cleaning section 10 as shown in FIG. 1A. The same features as already shown in FIG. 1A have the same reference numerals and reference is made to the description above. In the frontal view it can be seen that the first cleaning elements 111 and the second cleaning elements 121 are arranged in alternating rows. The first cleaning elements 111 form first rows 112 of first cleaning elements and the second cleaning elements 121 form second rows 122 of second cleaning elements. Here, three first rows 112, each having three double tufts, and three second rows 122, each having two double tufts, are alternately arranged in longitudinal direction. As shown here, the rows of cleaning elements may be centrically aligned in their rest position. Hence, during operation every other row of cleaning elements is set into an arcuate oscillation that occurs in a plane being essentially perpendicular to the longitudinal extension axis of the oral cleaning section 10. The second cleaning elements 121 extend through apertures 130 formed in the first carrier 110. The apertures 130 have a circumferential extension (here circumferential is meant with respect to the longitudinal extension axis L indicated by the dash-dotted line drawn in FIG. 1B; the aperture 130 needs not to be bent around the longitudinal extension axis) that is large enough to allow for the arcuate oscillation of the second cleaning elements 121, but the axial extension (in the longitudinal extension axis L) is only about as wide as the axial extension (here the axial extension is the width of the second cleaning elements 121 in the longitudinal extension direction) of the second cleaning elements 121 (here realized as bristle tufts) to allow for a high density of the cleaning elements in longitudinal direction. In other words, the embodiment supports achieving a minimal distance between the first and second rows 112 and 122 in the longitudinal direction, which leads to a high density of cleaning elements in longitudinal direction; this will be further discussed with reference to FIG. 3 and FIG. 4). The achieved density of cleaning elements in longitudinal direction is higher than the density that could be achieved on first and second carriers that are arranged side by side instead of on top of each other, as the mounting of cleaning elements such as bristle tufts requires a certain wall thickness of carrier material between mounting cavities to avoid the material breaking (or deforming) during the mounting process (for example, anchoring requires to have a wall thickness of about 0.8 mm or more).

The present disclosure may have a first and a second carrier 110 and 120 that are arranged on top of each other with respect to the extension direction of the cleaning elements such that the first and second carriers can move relatively to each other and can both laterally extend so that they overlap in at least a lateral direction. This allows for an overlap of the required walls between the mounting cavities so that in total a higher density of cleaning elements in longitudinal direction is achieved than with a side-by-side (non-overlapping) arrangement. It is to be noted that the shown embodiment is just exemplary. The basic feature relating to an aspect of the proposed oral cleaning section relies in the fact that a first carrier and a second carrier are arranged on top of each other (the first and second carriers thereby laterally overlapping). Only a single second cleaning element may be mounted on the cleaning side of the second carrier. The first and/or second cleaning elements may be arranged as individual elements, in rows, in arrays etc. The first and second cleaning elements may be arranged in alternating order or the second cleaning element or second cleaning elements may extend through a single aperture formed in the first carrier or through several apertures formed in the first carrier.

Figure 2:
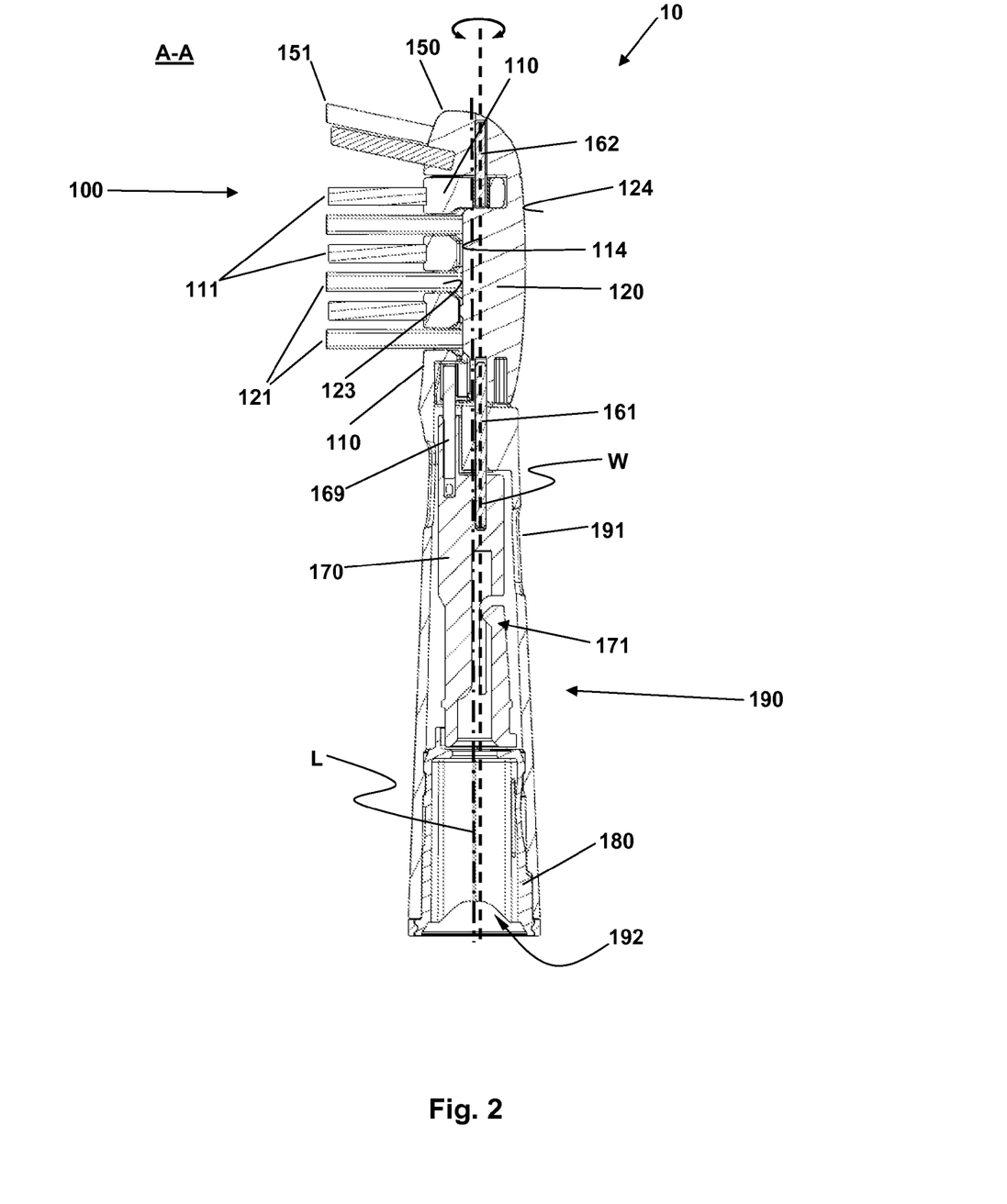
FIG. 2 is a longitudinal cross sectional cut through the oral cleaning section shown in FIG. 1B along line A-A.

FIG. 2 shows a longitudinal cross sectional cut through the oral cleaning section 10 as shown in FIG. 1B along line A-A. The tube 191 of the mounting structure 190 is essentially hollow and accommodates a sleeve 180 for clamping the oral cleaning section 10 onto a mount of a handle section of an oral cleaning device and a coupling element 170 for coupling the drive shaft of the oral cleaning device to the movably supported second carrier 120. The mount and the shaft of the handle section of the oral cleaning device are inserted into the hollow tube 191 through opening 192. The coupling element 170 comprises a snap-fit hook 171 having a substantially V-like nose that snaps into a substantially V-like groove formed in the shaft of the drive shaft to establish a detachable connection of the coupling element 170 and the shaft. Such a snap-hook fit is described in EP 0 500 537 B1, the disclosure of which is incorporated herein by reference. The sleeve 180 has a spring-like element that clamps onto the mount. The details of the sleeve 180 and of the coupling insert 170 are in more detail explained in U.S. Pat. No. 6,588,042 and EP 1 023 001 B1, the disclosure of which is incorporated herein by reference.

The coupling element 170 is coupled to the second carrier 120 via a coupling shaft 163, which coupling shaft 163 transfers a motion induced through the drive shaft of the oral cleaning device onto the coupling element 170 to the second carrier 120, so that an oscillatory wiping motion of the second carrier 120 essentially around a longitudinal axis W defined by the first and second bearing shafts 161 and 162 is effected during operation. The longitudinal axis W defined by the first and second bearing shafts 161 and 162 is essentially parallel to the longitudinal extension axis L of the oral cleaning section 10. In the shown exemplary embodiment, the second carrier 120 is integral with the third carrier 150, which third carrier 150 is hence also performing said oscillatory wiping motion during operation. The third carrier 150 is movably supported at the first carrier 110 via the second bearing shaft 162. As discussed above, the second cleaning elements 121 that are mounted on the cleaning side 123 of the second carrier 120 extend through apertures 130 formed in the first carrier 110 and thus form a high density cleaning element field together with the first cleaning elements 111 mounted on the cleaning side 113 (see FIG. 1A) of the first carrier 110 in close vicinity of the apertures 130. In the shown example, also the third cleaning elements 151 mounted on the cleaning side of the third carrier 150 are members of the cleaning elements field.

In the embodiment shown in FIG. 2 it can be seen that the second carrier 120 is arranged underneath the first carrier 110, i.e. the cleaning side 123 of the second carrier 120 is positioned underneath the second side 114 (being opposite to the cleaning side of the first carrier) of the first carrier 110, thus allowing for a lateral overlap of the first and second carriers 110 and 120.

Figure 3:
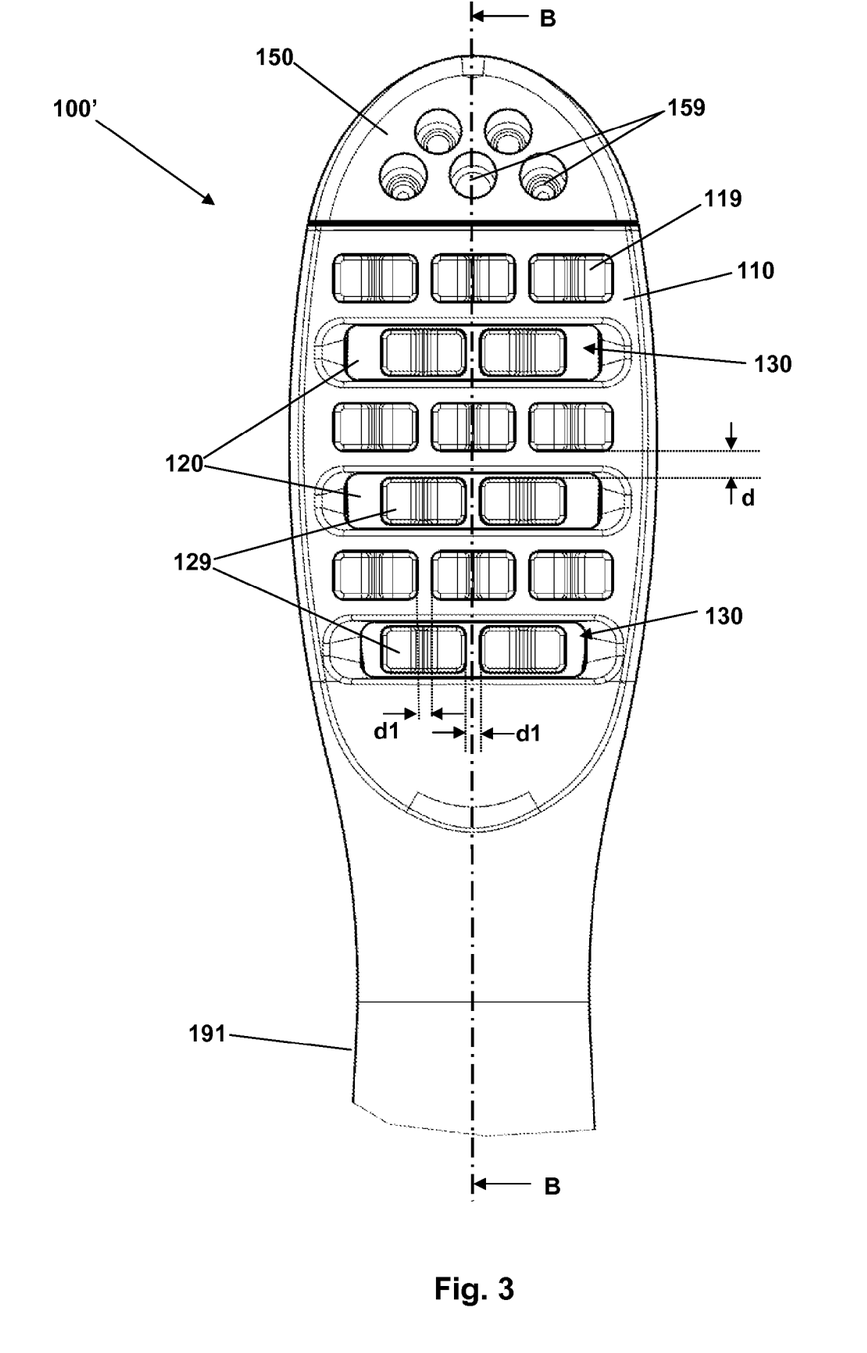
FIG. 3 is a frontal view onto the cleaning side of the head part of the oral cleaning section shown in FIG. 1B without mounted bristle tufts.

FIG. 3 shows a frontal view onto the cleaning side 113 of a "naked" head part 100' of the oral care section as was shown in FIG. 1B, but here shown without mounted cleaning elements. Thus, first mounting holes 119 for mounting of the first cleaning elements are visible in the first carrier 110, second mounting holes 129 for mounting the second cleaning elements are visible in the second carrier 120 through the apertures 130 formed in the first carrier 110, and third mounting holes 159 for mounting of the third cleaning elements are visible in the third carrier 150. The first mounting holes 119 and the second mounting holes 129 are realized as double tuft holes with a recessed bridge wall to enhance the density of cleaning elements in the row direction. Mounting holes subdivided into multiple segments are described in EP 1 138 222 B1, the content of which is included herein by way of reference. The vertical distance dl (which is the distance between the mounting holes measured in a plane perpendicular to the longitudinal extension axis that coincides with line B-B) between the double holes is here about 0.8 mm, which is required to ensure e.g. secure stapling of bristle tufts without the risk to break or strongly deform the intermediate walls. The total longitudinal distance d between the rows of cleaning elements is here about 1 mm due to a wall thickness of about 0.8 mm between the first mounting holes 119 and the wall of the apertures 130 and a small distance of about 0.2 mm between the second mounting holes 129 and the aperture walls (the latter distance allowing for a slight widening of, for example, bristle tufts that extend through the apertures 130).

In case the second carrier 120 would be arranged side-by-side with the first carrier 110 (whether the carriers would be arranged at the same height or one of the carriers being somewhat recessed), the minimal wall thickness of about 0.8 mm required for the second carrier would add to the wall thickness of about 0.8 mm required for the first carrier, so that a distance of at least about 1.6 mm would result between the rows of cleaning elements. A side-by-side arrangement of a first carrier and a second carrier is described in EP 2 107 892 A1, the content of which is included herein by way of reference. Hence, the proposed arrangement of second carrier 120 arranged underneath the first carrier 110 allows to increase the density of cleaning elements in the direction that is perpendicular to the row direction. The distance d between a row of first cleaning elements and a row of second cleaning elements can hence be made less than about 1.6 mm, the distance d can be made less than about 1.4 mm, less than about 1.2 mm and the distance d can be made to lie in the range of about 0.8-1.0 mm. In general, the distance between cleaning elements arranged on the first carrier and cleaning elements arranged on the second carrier can be made about as small as the distance between two cleaning elements arranged on only one of the two carriers due to the allowed lateral overlap between the first and second carriers arranged on top of each other.

Figure 4:
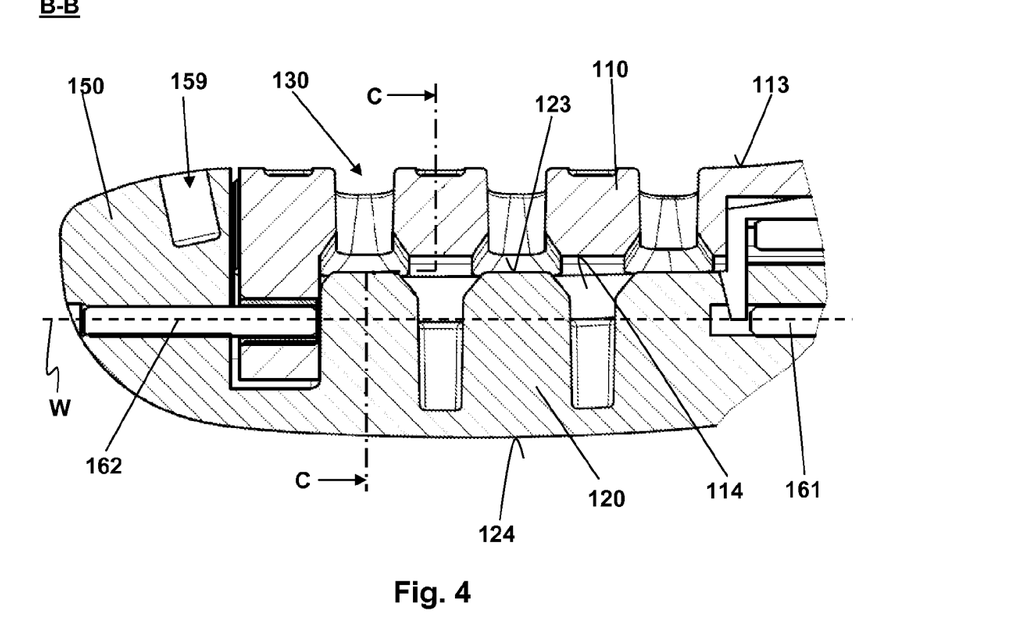
FIG. 4 is a longitudinal cross sectional cut through a front section of the head part of the oral cleaning section as shown in FIG. 3 along line B-B.

FIG. 4 shows a longitudinal cross sectional cut through a front section of the "naked" head part 100' as shown in FIG. 3 along the line B-B as indicated in FIG. 3. The second carrier 120 is movably supported at the first carrier 110 of the oral cleaning section via the first bearing shaft 161 and the second bearing shaft 162. The front part of the first bearing shaft 161 is secured to the second carrier 120. The second bearing shaft 162 extends in longitudinal direction and is secured to the third carrier 150 and is loosely extending into a bore formed in the first carrier 110 so that the second carrier 120 (and the third carrier 150 being integral with the second carrier 120) can pivot around the longitudinal axis W defined by the first bearing shaft 161 and the second bearing shaft 162. As the cross sectional cut goes through the walls between the second mounting holes, the second mounting holes are not visible. The cut goes also through the recessed bridge walls of the first mounting holes so that the first mounting holes are also not visible. A third mounting hole 159 is visible in this cross-sectional cut. Further, the apertures 130 are visible. In the mounted state, the second cleaning elements 121 extend through the apertures 130 as is shown in FIG. 2. The second carrier 120 has a second side 124 that is exposed at the back side of the head part. The second side 124 may be textured, for example, may be provided with a pattern of elastomeric elements suitable for tongue cleaning as is generally known in the art. As can be seen, the cleaning side 123 of the second carrier 120 laterally extends (here: in longitudinal direction) underneath the second side 114 of the first carrier 110 so that the first and second carriers 110 and 120 overlap in longitudinal direction.

Figure 5:
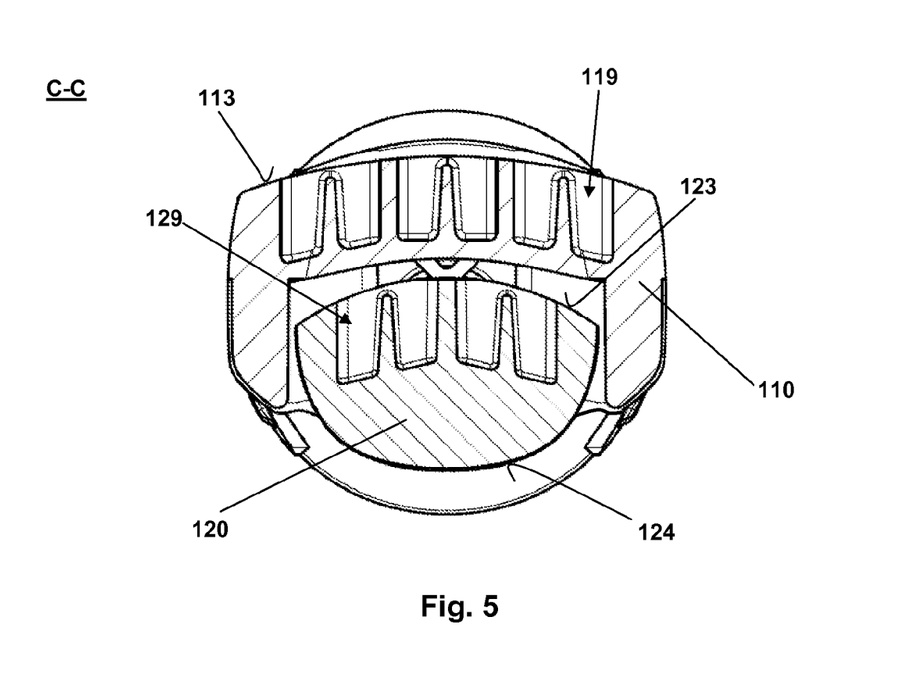
FIG. 5 is a staged cross sectional cut through the head part of the oral cleaning section as shown in FIG. 4 along line C-C.
Figure 6:
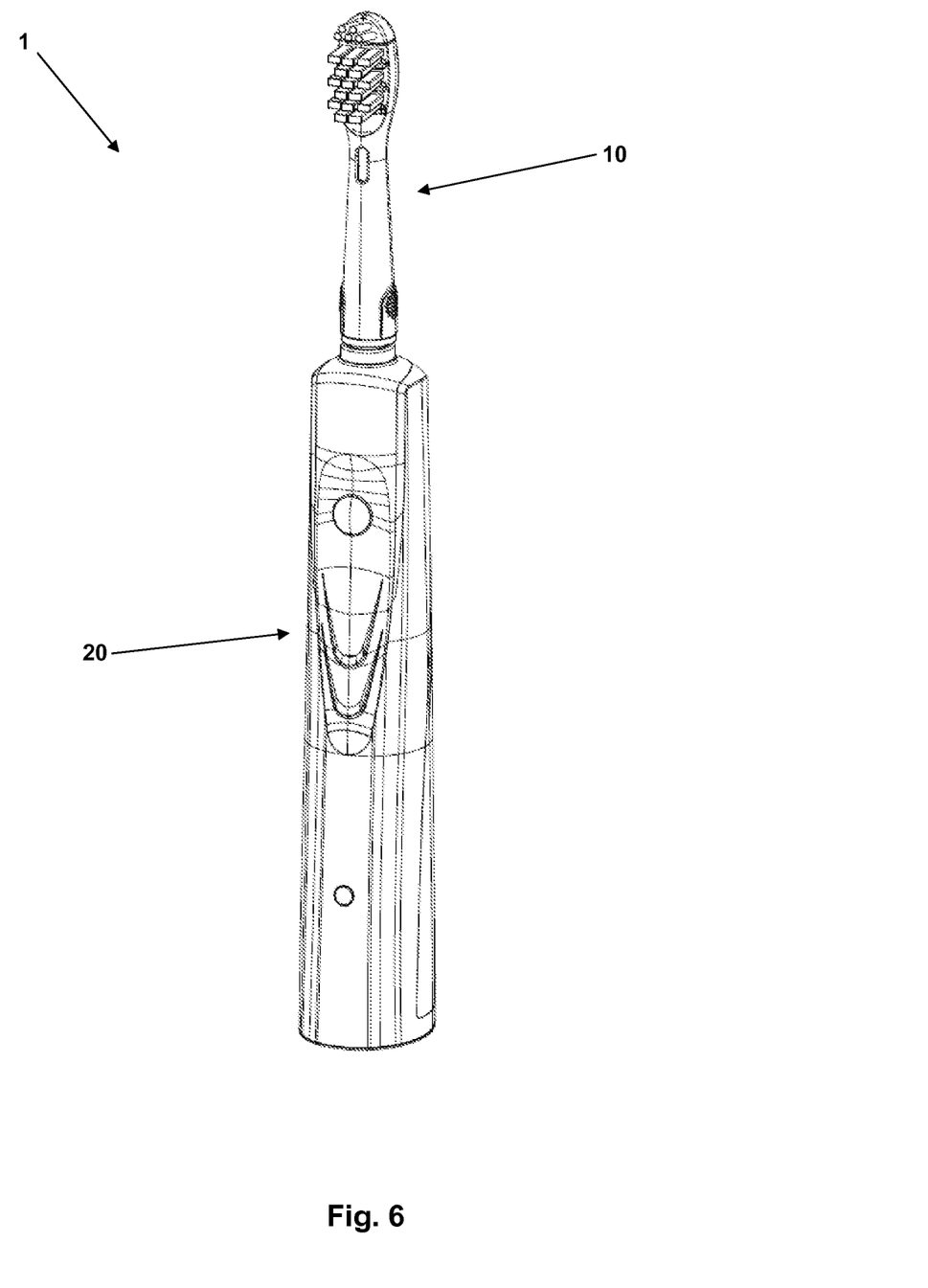
FIG. 6 is a perspective view onto an oral cleaning device realized as an electric toothbrush that comprises a detachable oral cleaning section as proposed.

FIG. 5 shows a stepped cross sectional cut through the head part of the oral cleaning section along line C-C as indicated in FIG. 4. Line C-C is stepped so that the cut goes through the first mounting holes 119 and the second mounting holes 129. The second carrier 120 is partially enveloped (i.e. enclosed) by the first carrier 110. The second side 124 of the second carrier 120 is exposed at the back side of the head part so that it can be brought into contact with tissue present in the oral cavity, e.g. the tongue. In another embodiment, the first carrier is fully enveloping the second carrier (i.e. the second carrier is fully housed inside the first carrier without the second side of the second carrier being exposed). FIG. 6 shows an oral cleaning device 1 realized as an electric toothbrush comprising a handle section 20 and an oral cleaning section 10 as proposed realized as a detachable brush head.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral cleaning section comprising:
a first carrier having a cleaning side on which at least a first cleaning element is mounted and a second side opposite to the cleaning side;
a second carrier having a cleaning side on which at least a second cleaning element is mounted; and
at least one aperture being formed in the first carrier such that the aperture extends from the cleaning side to the second side, with the second cleaning element extending through the aperture;
wherein the second carrier is arranged underneath the first carrier such that the cleaning side of the second carrier is underneath the second side of the first carrier and laterally extends beyond the aperture in at least a first direction; wherein the first carrier and the second carrier are arranged for relative movement to each other; and wherein the second carrier is arranged for an oscillatory wiping motion around a longitudinal axis (W) that is essentially parallel to a longitudinal extension axis (L) of the oral cleaning section.

2. The oral cleaning section according to claim 1, wherein the first carrier and the second carrier are movably coupled to each other.

3. The oral cleaning section according to claim 1, further comprising a coupling element for transferring a motion induced by a drive to at least one of the first carrier or the second carrier.

4. The oral cleaning section according to claim 1, wherein at least one of the first and second cleaning elements is a bristle or a bristle tuft.

5. The oral cleaning section according to claim 1, wherein at least a first row of first cleaning elements is mounted on the first carrier and at least a second row of second cleaning elements is mounted on the second carrier and the second row of second cleaning elements extends through the aperture.

6. The oral cleaning section according to claim 1, wherein a distance (d) between an outer edge of the first cleaning element and an outer edge of the second cleaning element is less than about 1.6 mm.

7. The oral cleaning section according to claim 1, wherein the oral cleaning section is a replacement brush head for detachable connection to a handle section of a toothbrush.

8. The oral cleaning section of claim 1, wherein the first carrier has at least two apertures and at least two second rows of second cleaning elements are mounted on the second carrier and each of the second rows of second cleaning elements extends through one of the two apertures.

9. An oral cleaning device comprising an oral cleaning section according to claim 1.

10. The oral cleaning device according to claim 9 that further comprises a handle section to which the oral cleaning section is detachably connected.

11. The oral cleaning device according to claim 9, wherein the device is an electric toothbrush.

12. An oral cleaning section comprising:
a first carrier having a cleaning side on which at least a first cleaning element is mounted and a second side opposite to the cleaning side;
a second carrier having a cleaning side on which at least a second cleaning element is mounted; and
at least one aperture being formed in the first carrier such that the aperture extends from the cleaning side to the second side, with the second cleaning element extending through the aperture;
wherein the second carrier is arranged underneath the first carrier such that the cleaning side of the second carrier is underneath the second side of the first carrier and laterally extends beyond the aperture in at least a first direction; wherein the first carrier and the second carrier are arranged for relative movement to each other; and wherein the first carrier is arranged to at least partially envelope the second carrier.

13. The oral cleaning section according to claim 12, wherein a second side of the second carrier forms an exterior surface of the oral cleaning section, the second side of the second carrier in particular being textured.

14. An oral cleaning section comprising:
- a first carrier having a cleaning side on which at least a first cleaning element is mounted and a second side opposite to the cleaning side;
- a second carrier having a cleaning side on which at least a second cleaning element is mounted; and
- at least one aperture being formed in the first carrier such that the aperture extends from the cleaning side to the second side, with the second cleaning element extending through the aperture;

wherein the second carrier is arranged underneath the first carrier such that the cleaning side of the second carrier is underneath the second side of the first carrier and laterally extends beyond the aperture in at least a first direction; wherein the first carrier and the second carrier are arranged for relative movement to each other; and wherein a third carrier concludes the oral cleaning section at the distal end and the third carrier is fixedly connected with the second carrier.

\* \* \* \* \*